United States Patent [19]

Guntaka et al.

[11] Patent Number: 5,780,611
[45] Date of Patent: Jul. 14, 1998

[54] OLIGOMERS WHICH INHIBIT EXPRESSION OF COLLAGEN GENES

[75] Inventors: Ramareddy V. Guntaka; Karl Theodore Weber. both of Columbia; Attila Kovacs. St. Louis; Jagannadhachari Kandala. Columbia. all of Mo.

[73] Assignee: Ramareddy Venkata Guntaka. Columbia. Mo.

[21] Appl. No.: 802,547

[22] Filed: Feb. 18, 1997

Related U.S. Application Data

[63] Continuation-in-part of Ser. No. 712,357, Sep. 11, 1996, which is a continuation-in-part of Ser. No. 528,836, Sep. 15, 1995, abandoned.

[51] Int. Cl.[6] .............................. C12Q 1/68; C07H 21/04
[52] U.S. Cl. .................. 536/24.5; 536/23.1; 435/6; 435/91.1; 435/172.1; 435/172.3; 435/320.1; 435/325; 435/366
[58] Field of Search ................... 435/6, 91.1, 172.1, 435/172.3, 325, 366; 536/23.1, 24.5; 514/44

[56] References Cited

FOREIGN PATENT DOCUMENTS

| 375408 | 6/1990 | European Pat. Off. |
| 9411494 | 5/1994 | WIPO |

OTHER PUBLICATIONS

Khillan et al. PNAS 91: 6298–6302 (1994).
Laptev et al. Biochemistry 33: 11033–11039 (1994).
Colige et al. Biochemistry 32: 711 (1993).
Shi et al. Circulation 90: 944–951 (1994).
Gewirtz et al. PNAS 93: 3161–3163 (1996).
Stall et al. Pharm. Res. 12: 465–483 (1995).
Rojanasakul Adv. Drug. Delivery. Reviews 18: 115–131 (1996).
Ing et al.; Nucleic Acids Research; 21:2789–2796 (1993).
Giovannangeli et al.; Proc. Natl. Acad. Sci.; 89:8631–8635 (1992).
Young et al.; Biochemistry; 88:10023–10026 (1991.
Rando et al.; Nucleic Acids Research; 22:678–685 (1994).
Gee et al.; J. Bio. Chem.; 267:11163–11167 (1992.
Tung et al.; Nucleic Acids Research; 21:5489–5494 (1993).
Degols et al.; J. Bio. Chem.; 269:16933–16937 (1994).
Kamenetskii et al.; Annu. Rev. Biochem.; 64:65–95 (1995).
Maher; BioEssays; vol. 14 (1992).
Prockop et al.; Annu. Rev. Biochem.; 64:403–434 (1995).
Uhlmann et al.; Chemical Reviews; 90(4):543–584 (1990).
Tseng et al.; Cancer Gene Therapy; 1(1):65–71 (1994).
Helene; Anticancer Drug Design; 6:569–584 (1991).
Kandimalla et al.; Gene; 149:115–121 (1994).

*Primary Examiner*—John L. LeGuyader
*Attorney, Agent, or Firm*—Hovey. Williams. Timmons & Collins

[57] ABSTRACT

Oligomers which inhibit expression of a collagen gene are described. It is believed that each oligomer, when introduced into a cell, forms a transcription-inhibiting complex composed of the oligomer and the collagen-gene promoter region. The oligomer, preferably a phosphorothioate deoxyoligonucleotide, preferably binds in the antiparallel orientation to the polypurine strand of a polypurine-polypyrimidine region of the promoter region of a mammalian $\alpha 1$ (I) collagen gene.

6 Claims, 9 Drawing Sheets

```
                                      Oligo Control (SEQ ID NO: 7)
                                      5'-[CAAG GGTGGCAGAA TTGCAA]-3'

Bgl II                                                                            Oligo C-2 (SEQ ID NO: 2)
-230                                    Oligo C-3 (SEQ ID NO: 3)
5'- ATGTAGATCT GGGGGACAAG GGTGGCAGAA TT[GCAAAGGG GGGAGGGGGC TGGGTGGACT]-3'
3'- TACATCTAGA CCCCCTGTTC CCACCGTCTT AA]CGTTTCCC CCCTCCCCCG ACCCACCTGA-5'
           *                                          ────── ──────
                                                    f    e    d    c
                                                       Hae III -170                       Oligo C-1 (SEQ ID NO: 1)
5'-[CCTTTCCCTT CCTTTCCCTC CTCCCCCCTC] TTCGTTCCAA ATTGGGGGCC-3' ⎫
3'-[GGAAAGGGAA GGAAAGGGAG GAGGGGGGAG] AAGCAAGGTT TAACCCCCGG-5' ⎬ (SEQ ID NO: 4)
      ──────────                                              ⎭
         a
         b Oligo Col TFO (SEQ ID NO: 5)
3'-[GGAAAGGGAA GGAAAGGGAG GAGGGGGGAG]-5'

Oligo Col TFOa (SEQ ID NO: 6)
5'-[GGAAAGGGAA GGAAAGGGAG GAGGGGGGAG]-3'
```

FIG. 1.

Oligo Col TFO (SEQ ID NO: 5)

3'- GGAAAGGGAA GGAAAGGGAG GAGGGGGGAG -5'

Oligo Col TFOa (SEQ ID NO: 6)

5'- GGAAAGGGAA GGAAAGGGAG GAGGGGGGAG -3'

Oligo 147 P (SEQ ID NO: 8)

3'- GGAA GGAAAGGGAG GAGG -5'

Oligo 170 APS (SEQ ID NO: 9)

5'- GGAAAGGGAA GGAAAGGG -3'

Oligo 164 AP (SEQ ID NO: 10)
Oligo 164 APS (SEQ ID NO: 11)

5'- GGAA GGAAAGGGAG GAGG -3'

Oligo 158 APS (SEQ ID NO: 12)

5'- AAAGGGAG GAGGGGGGAG -3'

*FIG. 8.*

(SEQ ID NO: 13)

```
      165 —                                                    — 136
5' — TCCCTTCCCT CCTCCTCCCC CTCTCCATTC — 3'
3' — AGGGAAGGGA GGAGGAGGGG GAGAGGTAAG — 5'
```

*Fig. 12.*

(SEQ ID NO: 14)

```
5' — AGGGAAGGGA GGAGGAGGGG GAGAGGTAAG — 3'
```

*Fig. 13.*

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 30 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO (i v) ANTI-SENSE: NO (v i i i) POSITION IN GENOME:
    (C) UNITS: bp (x i) SEQUENCE DESCRIPTION: SEQ ID NO:1:

CCTTTCCCTT CCTTTCCCTC CTCCCCCCTC                           30

(2) INFORMATION FOR SEQ ID NO:2:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (i i) MOLECULE TYPE: DNA (genomic)

(i i i) HYPOTHETICAL: NO (i v) ANTI-SENSE: NO (v i i i) POSITION IN GENOME:
        (C) UNITS: bp (x i) SEQUENCE DESCRIPTION: SEQ ID NO:2:

GCAAAGGGGG GAGGGGGCTG GGTGGA                               26

(2) INFORMATION FOR SEQ ID NO:3:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (i i) MOLECULE TYPE: DNA (genomic)

(i i i) HYPOTHETICAL: NO (i v) ANTI-SENSE: NO (v i i i) POSITION IN GENOME:
        (C) UNITS: bp (x i) SEQUENCE DESCRIPTION: SEQ ID NO:3:

CAAGGGTGGC AGAATTGCAA                                      20

(2) INFORMATION FOR SEQ ID NO:4:

(i) SEQUENCE CHARACTERISTICS:
        (A) LENGTH: 110 base pairs
        (B) TYPE: nucleic acid
        (C) STRANDEDNESS: double
        (D) TOPOLOGY: linear (i i) MOLECULE TYPE: DNA (genomic)

(i i i) HYPOTHETICAL: NO (i v) ANTI-SENSE: NO (v i i i) POSITION IN GENOME:
        (C) UNITS: bp (x i) SEQUENCE DESCRIPTION: SEQ ID NO:4:

ATGTAGATCT GGGGGACAAG GGTGGCAGAA TTGCAAAGGG GGGAGGGGGC TGGGTGGACT    60
CCTTTCCCTT CCTTTCCCTC CTCCCCCCTC TTCGTTCCAA ATTGGGGGCC              110

(2) INFORMATION FOR SEQ ID NO:5:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: YES ( v i i i ) POSITION IN GENOME:
    ( C ) UNITS: bp ( x i ) SEQUENCE DESCRIPTION: SEQ ID NO:5:

GAGGGGGGAG GAGGGAAAGG AAGGGAAAGG                30

( 2 ) INFORMATION FOR SEQ ID NO:6:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( v i i i ) POSITION IN GENOME:
        ( C ) UNITS: bp ( x i ) SEQUENCE DESCRIPTION: SEQ ID NO:6:

GGAAAGGGAA GGAAAGGGAG GAGGGGGGAG                30

( 2 ) INFORMATION FOR SEQ ID NO:7:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( v i i i ) POSITION IN GENOME:
        ( C ) UNITS: bp ( x i ) SEQUENCE DESCRIPTION: SEQ ID NO:7:

CAAGGGTGGC AGAATTGCAA                           20

( 2 ) INFORMATION FOR SEQ ID NO:8:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( v i i i ) POSITION IN GENOME:
        ( C ) UNITS: bp ( x i ) SEQUENCE DESCRIPTION: SEQ ID NO:8:

GGAAGGAAAG GGAGGAGG                                                                                                   18

( 2 ) INFORMATION FOR SEQ ID NO:9:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( v i i i ) POSITION IN GENOME:
        ( C ) UNITS: bp ( x i ) SEQUENCE DESCRIPTION: SEQ ID NO:9:

GGAAAGGGAA GGAAAGGG                                                                                                   18

( 2 ) INFORMATION FOR SEQ ID NO:10:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( v i i i ) POSITION IN GENOME:
        ( C ) UNITS: bp ( x i ) SEQUENCE DESCRIPTION: SEQ ID NO:10:

GGAAGGAAAG GGAGGAGG                                                                                                   18

( 2 ) INFORMATION FOR SEQ ID NO:11:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( v i i i ) POSITION IN GENOME:
        ( C ) UNITS: bp ( x i ) SEQUENCE DESCRIPTION: SEQ ID NO:11:

GGAAGGAAAG GGAGGAGG                                                                                                   18

( 2 ) INFORMATION FOR SEQ ID NO:12:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear -continued (  i  i  ) MOLECULE TYPE: DNA (genomic)

(  i  i  i  ) HYPOTHETICAL: NO (  i  v  ) ANTI-SENSE: YES (  v  i  i  i  ) POSITION IN GENOME:
          ( C ) UNITS: bp (  x  i  ) SEQUENCE DESCRIPTION: SEQ ID NO:12:

AAAGGGAGGA GGGGGGAG                                                               18

( 2 ) INFORMATION FOR SEQ ID NO:13:

(  i  ) SEQUENCE CHARACTERISTICS:
          ( A ) LENGTH: 30 base pairs
          ( B ) TYPE: nucleic acid
          ( C ) STRANDEDNESS: double
          ( D ) TOPOLOGY: linear (  i  i  ) MOLECULE TYPE: DNA (genomic)

(  i  i  i  ) HYPOTHETICAL: NO (  i  v  ) ANTI-SENSE: NO (  v  i  i  i  ) POSITION IN GENOME:
          ( C ) UNITS: bp (  x  i  ) SEQUENCE DESCRIPTION: SEQ ID NO:13:

TCCCTTCCCT CCTCCTCCCC CTCTCCATTC                                                  30

( 2 ) INFORMATION FOR SEQ ID NO:14:

(  i  ) SEQUENCE CHARACTERISTICS:
          ( A ) LENGTH: 30 base pairs
          ( B ) TYPE: nucleic acid
          ( C ) STRANDEDNESS: single
          ( D ) TOPOLOGY: linear (  i  i  ) MOLECULE TYPE: DNA (genomic)

(  i  i  i  ) HYPOTHETICAL: NO (  i  v  ) ANTI-SENSE: YES (  v  i  i  i  ) POSITION IN GENOME:
          ( C ) UNITS: bp (  x  i  ) SEQUENCE DESCRIPTION: SEQ ID NO:14:

AGGGAAGGGA GGAGGAGGGG GAGAGGTAAG                                                  30

OLIGOMERS WHICH INHIBIT EXPRESSION OF COLLAGEN GENES

RELATED APPLICATION

This is a continuation-in-part of application Ser. No. 08/712,357, filed Sep. 11, 1996, which is a continuation-in-part of application Ser. No. 08/528,836, filed Sep. 15, 1995 now abandoned.

SEQUENCE LISTING

A printed Sequence Listing accompanies this application, and also has been submitted with identical contents in the form of a computer-readable ASCII file on a floppy diskette.

BACKGROUND OF THE INVENTION

1. Field of the Invention

The present invention is broadly concerned with oligomers capable of inhibiting expression of collagen genes, and corresponding methods. More particularly, the invention pertains to transcription-inhibiting complexes, each composed of an oligomer bound to a polypurine-polypyrimidine region of a collagen-gene promoter region.

2. Description of the Prior Art

Collagen is a family of fibrous proteins present in all multicellular organisms. It is the major fibrous element of skin, bone, tendon, cartilage, blood vessels, and teeth, and is present in nearly all organs. Collagen is composed of a triple-helix formed from three polypeptide chains. These triple helices are wrapped around each other to form a super helix. In several types of collagen, including Type I collagen, these super helixes form fibrils. In the case of Type I collagen, the polypeptide triple helix is composed of two $\alpha 1$ polypeptide chains and one $\alpha 2$ polypeptide chain.

In response to tissue injury or invasion, a healing response is invoked that ultimately leads to an accumulation of fibrillar type I collagen. This is true for many systemic organs and the heart. Such a healing response, when unabated and invoked in the absence of injury, leads to a progressive interstitial fibrosis that proves pathologic. Parenchymal cell function is compromised by a disproportionate concentration of type I collagen, a characteristic feature of interstitial fibrosis in different organs (1–9). Various stages of organ dysfunction are marked by the activation and repression of type I collagen genes, thereby allowing for the design of specific agents to promote the necessary or adaptive phenotype or to repress the onset of pathologic interstitial fibrosis.

A wide array of hormones, cytokines, and growth factors have been implicated in the mediation of fibrous tissue formation (10–20). Many of these factors mediate their action through transcriptional mechanisms. Therefore, the study of transcriptional regulatory elements within the $\alpha 1(I)$ and $\alpha 2(I)$ collagen gene promoters and their transacting protein factors is of major interest. Effector cells which bring about fibrosis include interstitial fibroblasts and phenotypically transformed fibroblast-like cells termed myofibroblasts (21).

Several cis-acting elements in the $\alpha 1(I)$ and $\alpha 2(I)$ collagen genes located on both sides of the transcription start site as well as their transacting factors have been identified (for reviews, see 22–24). Very little is known about the factor(s) binding to the −200 to −140 region of the $\alpha 1(I)$ collagen promoter. These sequences are highly conserved among mammals (25), and correspond to the DNase I hypersensitive regions around the transcriptional start site. It is generally believed that DNase I hypersensitivity represents nucleosome-free regions which can interact with various regulatory proteins (26). Cis-acting elements in the −190 to −170, and −160 to −133 regions of the mouse $\alpha 1(I)$ promoter and trans-acting factors binding to these elements in NIH-3T3 fibroblast nuclear extracts have been studied in some detail (271). Competition experiments in EMSA's provided evidence that a single factor binds to both of these elements. Furthermore, in transient transfection experiments, while a three-bp substitution mutation in the more distal element (from −194 to −168) had little effect on the promoter activity, a three-bp mutation in the more proximal element (from −160 to 133) resulted in a four-fold increase in reporter gene expression, indicating that this factor negatively regulates transcription (designated IF-1 in 26). In contrast, Brenner et al. (28) have shown that deletion of both regions of the mouse $\alpha 1(I)$ promoter resulted in decreased promoter activity implying positive activation of transcription.

Oligomers (i.e., oligonucleotides and oligonucleotide analogs such as protein nucleic acid) are reagents for inhibition of gene expression because of their high-affinity binding to specific nucleotide sequences. The best known strategy for oligomer reagents involves antisense oligonucleotides which bind mRNA to inhibit its processing or translation. For example, Laptev et al. (44) showed that the expression of the human $\alpha 1(I)$ collagen gene is effectively inhibited by antisense oligonucleotides targeted at specific regions of the $\alpha 1(I)$ mRNA. Additionally, gene promoters can serve as targets for a novel, antisense strategy, namely the triplex strategy (for reviews, see 40 and 45). This strategy employs single-stranded oligomers that bind to the major groove of a polypurine-polypyrimidine region of a double-stranded DNA to form a triple helix in a sequence-specific manner. These oligomers are called triplex-forming oligonucleotides (TFO's) or TFO analogs. In a polypurine-polypyrimidine region, a purine-rich DNA single strand is hydrogen bonded by Watson-Crick base-pairing to a pyrimidine-rich DNA single strand; the polypurine-polypyrimidine region is not necessarily a homopurine-homopyrimidine region in that the purine-rich DNA single strand may contain at least one pyrimidine residue and the pyrimidine-rich DNA single strand may contain at least one purine residue. These triplexes have been shown to inhibit sequence-specific DNA-binding proteins thereby affecting the transcriptional activity of various promoters in both in vitro and in vivo experiments (29–32). However, the use of oligomers to inhibit transcription of a collagen gene is unknown in the prior art.

SUMMARY OF THE INVENTION

The present invention provides a novel therapy for pathological fibrosis associated with medical conditions including but not limited to myocardial fibrosis in hypertensive heart diseases, atherosclerosis, restenosis, liver cirrhosis, lung fibrosis, and skin fibrosis found in scleroderma, in hypertrophic scars, and in skin following burn injury. In this therapy, expression of collagen genes is inhibited. A sequence-specific oligomer is introduced into a cell resulting in the production of a transcription-inhibiting complex composed of the oligomer bound to the promoter region of the collagen gene. These oligomers include but are not limited to phosphodiester, phosphorothioate, methylphosphonate, and methylphosphonothioate oligonucleotides, and oligonucleotide analogs such as protein nucleic acid. Oligomers can be formulated into pharmaceutically acceptable preparations including but not limited to injectable preparations, sprays, ointments, creams, gels, tablets, and perfusions.

In preferred embodiments, the oligomer is a phosphorothioate oligodeoxynucleotide having a length of at least 5 nucleotides, preferably from about 5 to 50 nucleotides. This oligonucleotide preferably binds in the antiparallel orientation to the polypurine strand of a polypurine-polypyrimidine region of the promoter region of a mammalian α1(I) collagen gene.

An especially preferred oligonucleotide (SEQ ID No: 13) is an anti-sense 30-mer oligonucleotide capable of bonding with the double-stranded promoter region of the human α1(I) collagen gene (SEQ ID No: 14) to form a triple complex.

BRIEF DESCRIPTION OF THE DRAWINGS

FIG. 1 is a diagram showing the sequences of the −230 to −120 portion of the rat α1(I) collagen promoter and some of the oligonucleotides used in this study. Restriction enzyme recognition sites are marked. The asterisk indicates the site of radiolabeling in DNase I footprinting experiments. The double-stranded oligonucleotides in boxes were used in electrophoretic mobility shift assays (EMSA's). The underlined sequences marked a through f correspond to the protected areas seen in DNase I footprinting studies. Arrowheads indicate sites of substitution mutations used in the study by Karsenty & de Crombrugghe (27). Single-stranded oligonucleotides Oligo Col TFO (SEQ ID No: 5), Oligo Col TFOa (SEQ ID No: 6), Oligo Control (SEQ ID No: 7), and double-stranded Oligo C-1 (SEQ ID No: 1) were used in triple-helix experiments;

FIG. 8 is a diagram showing some of the oligonucleotides used in this study. Single-stranded oligonucleotides Oligo Col TFO (SEQ ID No: 5), Oligo Col TFOa (SEQ ID No: 6), Oligo Col 147 P (SEQ ID No: 8), Oligo 170 APS (SEQ ID No: 9), Oligo 164 AP (SEQ ID No: 10), Oligo 164 APS (SEQ ID No: 11), and Oligo 158 APS (SEQ ID No: 12) were used in experiments to determine if each was capable of forming a triplex with double-stranded Oligo C-1 (SEQ ID No: 1);

FIG. 12 is a diagram showing the double-stranded sequence of the −165 to −136 portion of the human α1(a) collagen gene promoter region (SEQ ID No: 13)

FIG. 13. is a diagram of an anti-parallel oligonucleotide sequence (SEQ ID No: 14) which binds and forms a TFO with the FIG. 12 sequence.

DETAILED DESCRIPTION OF THE PREFERRED EMBODIMENT

Figure 2:
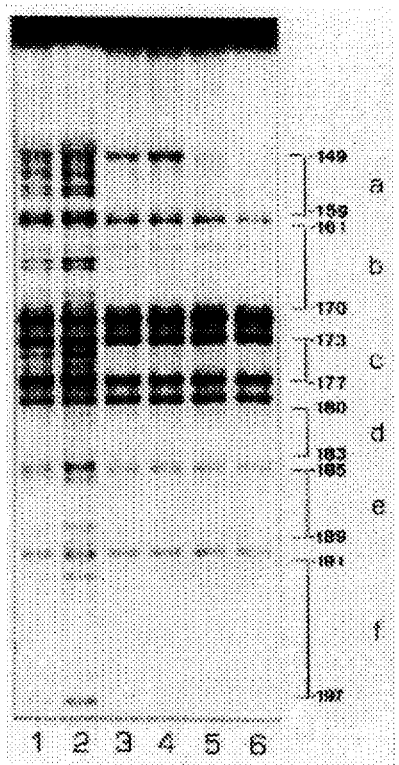
FIG. 2 shows an autoradiogram of a gel illustrating the DNase I footprint of a segment of the rat α1(I) collagen promoter. The BglII-HaeIII restriction fragment of SEQ ID No: 4 (−225 to −123) of plasmid pCol 952/1000labeled at the 3″ end of the noncoding strand was incubated without or with nuclear extracts of rat cardiac fibroblasts (RCF) and HeLa cells, and was treated with DNase I for 30 sec (lane 1) or 1 min (lane 2) in the absence of nuclear extracts; lanes 3–4 each contain 30 μg of RCF nuclear extracts, and DNase I digestion was for 1 or 2 min, respectively; lanes 5–6 each contain 30 μg of HeLa nuclear extracts, and DNase I digestion was for 1 or 2 min, respectively. Different areas of protection are marked by brackets. Numbers on the right correspond to base pairs upstream of the start of transcription.

The following examples describe preferred techniques for the synthesis of the therapeutic oligomers of the invention, and use thereof in the inhibition of collagen-gene expression; it is to be understood, however, that these examples are provided by way of illustration only, and nothing therein should be taken as a limitation upon the overall scope of the invention.

EXAMPLE 1

Oligonucleotide Synthesis and Preparation

Table 1 describes the oligonucleotides used in this study

| Oligonucleotide | Sequence ID No. | Strandedness | Type |
|---|---|---|---|
| Oligo C-1 | 1 | double | phosphodiester |
| Oligo C-2 | 2 | double | phosphodiester |
| Oligo C-3 | 3 | double | phosphodiester |
| Oligo Col TFO | 5 | single | phosphodiester |
| Oligo Col TFOa | 6 | single | phosphodiester |
| Oligo Control | 7 | single | phosphodiester |
| Oligo 147 P | 8 | single | phosphodiester |
| Oligo 170 APS | 9 | single | phosphorothioate |
| Oligo 164 AP | 10 | single | phosphodiester |
| Oligo 164 APS | 11 | single | phosphorothioate |
| Oligo 158 APS | 12 | single | phosphorothioate |

Phosphodiester oligonucleotides used were synthesized on an Applied Biosystems 381A DNA synthesizer at the DNA Core Laboratory of the University of Missouri-Columbia. Phosphorothioate oligonucleotides used were synthesized using a 392 DNA synthesizer (Applied Biosystems, Foster City, Calif.). Phosphodiester and phosphorothioate oligonucleotides were gel purified on a 6% polyacrylamide gel, electroeluted, and precipitated with ethanol. Double-stranded oligonucleotides were prepared by mixing equal amounts of complementary single strands in the presence of 0.25M NaCl. The mixture was heated to 80° C. for 5 min, incubated at 55° C. for 30 min, and then at 42° C. for 30 min. Alternatively, double-stranded oligonucleotides were prepared by mixing equal amounts of complementary single strands, heating the mixture at 80° C. for 5 minutes in 0.25M NaCl, followed by slow cooling to room temperature. The resulting double-stranded oligonucleotides were gel purified on a 6% or 10% polyacrylamide gel, eluted, and concentrated by ethanol precipitation.

EXAMPLE 2

Cloning of the Rat α1(I) Promoter Segment

A 1.1-kb fragment of the rat α1(I) collagen promoter was isolated by the PCR technique. Based on published sequence data, (33) specific 20- to 30-mer oligonucleotides were synthesized corresponding to −1000 and +100 regions of the α1(I) collagen gene. Rat genomic DNA was used as template. The PCR product was cloned into the HincII site of pGEM 3Z vector (Promega, Madison, Wis.) and was used for further subcloning (pCol 1.1). The accuracy of the clone was determined by restriction enzyme analysis and by DNA sequencing, which was done by the dideoxy method (34). A 900-bp fragment of the cytomegalovirus immediate early gene (CMV IE, −600 to +300) was isolated and subcloned from pCMV-NEO (Dr. M. Linial, Fred Hutchinson Cancer Rsch. Ct., Seattle, Wash.) and subcloned into the pGEM 3Z vector.

EXAMPLE 3

Plasmid Constructions

Plasmid pColCAT220 was constructed as follows: pCol 952/1000 was digested with XbaI and BglII, which release a 338-bp fragment of the rat α1(I) gene (−225 to +113). This fragment was cloned into the XbaI-BamHI site of the pCAT Basic vector (Promega, Madison, Wis.). To construct plasmid pCol140 the pColCAT220 plasmid was digested with EarI, the ends of the fragments were filled-in and were digested with XbaI. The resulting 249-bp fragment (−136 to +113) was isolated and inserted into the XbaI-HincII site of pGEM 4Z vector (Promega, Madison, Wis.). Plasmid pCol-CAT 140 was constructed by isolating the XbaI-HindIII fragment of plasmid pCol140 which contains the −136 to +113 sequence of rat α1(I) gene, and cloning into the XbaI-HindII site of pCAT Basic vector. Plasmid DNA for transfection was prepared by the alkaline lysis method followed by CsCl-ethidium bromide gradient centrifugation.

EXAMPLE 4

Gel Mobility Shift Analysis of Triple-Helix Formation

Target oligonucleotide Oligo C-1 (SEQ ID No: 1) was end-labeled with $[\alpha^{32}P]ATP$ using $T_4$ polynucleotide kinase, and was purified through a Sephadex G25 or G50 column. Approximately 5,000 to 10,000 cpm (0.6 ng) was incubated with increasing concentrations of Oligo Col TFO (SEQ ID No: 5) (final concentrations from 0 to ≈250 µM), Oligo Col TFOa (SEQ ID No: 6) (final concentrations from 0 to ≈25 µM), Oligo Control (SEQ ID No: 7) (final concentrations from 0 to ≈250 µM), Oligo 147 P (SEQ ID No: 8) (final concentrations from 0 to ≈6 µM), Oligo 170 APS (SEQ ID No: 9) (final concentrations from 0 to ≈0.25 µM), Oligo 164 AP (SEQ ID No: 10) (final concentrations from 0 to ≈4 µM), Oligo 164 APS (SEQ ID No: 11) (final concentrations from 0 to ≈0.25 µM), and Oligo 158 APS (SEQ ID No: 12) (final concentrations from 0 to ≈0.25 µM) in a binding buffer (TFO binding buffer) consisting of 20 mM Tris-HCl (pH 7.4), 20 mM $MgCl_2$, 2.5 mM spermidine, 10% sucrose, 0.25 mg/ml bovine serum albumin, and incubated at 22° C. for 60 min. Samples were electrophoresed through 8% polyacrylamide, 0.25% bisacrylamide gels or 10% polyacrylamide, 0.32% bisacrylamide gels buffered with 89 mM Tris, 89 mM boric acid (pH 7.5), and 20 mM $MgCl_2$ for 4.5 to 7 h at 10 V/cm at 6° C. Gels were then dried and autoradiographed.

EXAMPLE 5

Nuclear Extract Preparation

Adult rat cardiac fibroblasts (RCF) were grown in Dulbecco's modified Eagle's medium supplemented with 10% fetal calf serum, penicillin, streptomycin and incubated in 8% $CO_2$ atmosphere at 37° C. Cells were grown to subconfluency, and the medium was changed the night before preparation. Nuclear proteins were extracted using a variation of the method of Dignam et al. (35). All steps were carried out at 4° C. Cells were washed twice with cold PBS, harvested by scraping and pelleted (1250×g, 10 min). They were washed with 10 volumes of PBS and centrifuged as described above. Cells were next suspended in 10 packed volumes of Nonidet P-40 lysis buffer [0.6% Nonidet P-40, 0.15M NaCl, 10 mM Tris-HCl (pH 7.9), 1 mM EDTA] and incubated for 5 min. The nuclei were pelleted (1250×g, 10 min), washed with 5 volumes of lysis buffer and again centrifuged. Nuclear proteins were extracted from pelleted nuclei in an equal volume of cold extraction buffer [50 mM HEPES (pH 7.9), 0.5 mM EDTA, 0.75 mM $MgCl_2$, 500 mM KCl, 1 mM dithiothreitol, 0.1 mM phenylmethylsulphonyl fluoride, 2 µg/ml leupeptine, and 12.5% (vv) glycerol]. The suspension was dounced with 8 strokes of Kontes glass homogenizer (B type pestle). The resulting solution was stirred gently with a magnetic stirring bar for 30 min and centrifuged for 45 min at 26000×g. The supernatant was dialyzed against 50 volumes of storage buffer [20 mM HEPES (pH 7.9), 100 mM KCl, 0.2 mM EDTA, 0.5 mM phenylmethylsulphonyl fluoride, 20% glycerol]. The dialysate was centrifuged at 26000×g for 45 min and the supernatant containing the extract was aliquoted and stored in liquid nitrogen. Protein concentration was determined by the method of Bradford (36) using Bio-Rad reagent (Bio-Rad, Hercules, Calif.), as described by the supplier. HeLa nuclear extracts were prepared by the original Dignam method (35).

EXAMPLE 6

DNase I Footprinting

DNA binding reactions were performed in a final volume of 25 µl. A 100-bp fragment of the rat α1(I) collagen gene (−225 to −123) with BglII and HaeIII ends isolated from pCol 952/1000 (BglII-HaeIII restriction fragment of SEQ ID No: 4) was labeled with $(\alpha^{-32}P)ATP$ at the BglII site using the Klenow fragment of E. coli DNA polymerase I. Thirty fmol were incubated in a mixture containing 25 mM Tris-HCl (pH 7.5), 0.05 mM EDTA, 50 mM KCl, 1 mM dithio-threitol, 5% glycerol, and 2 µg of poly(dI:dC). Six µl of nuclear extract (30 µg protein) or buffer were added and the binding reaction was allowed to proceed on ice for 30 min. Ten µg/ml DNase I stock was freshly diluted in 60 mM $MgCl_2$ and 10 mM $CaCl_2$. Five µl (2.5 ng DNase I) were added to the binding reaction and incubated for 30 sec, 1 min, and 2 min for various samples at room temperature. The reaction was stopped with 50 µl of stop mix containing 200 mM NaCl, 20 mM EDTA, 1% sodium dodecyl sulfate, and 250 µg/ml yeast RNA, extracted once with phenol, once with phenolchloroform (1:1), and ethanol precipitated. The precipitates were collected by centrifugation, dried, and resuspended in 70% formamide buffer. The samples were then heat-denatured and loaded on a 8% acrylamide, 7M urea gel. Radioactive oligonucleotides were used as size markers. Gels were dried and autoradiographed at −70° C. with an intensifying screen.

EXAMPLE 7

Electrophoretic Mobility Shift Assays a) Two µl of RCF nuclear extracts (≈10 µg of protein) were incubated with approximately 20,000 cpm (10 fmol) of end-labeled oligonucleotides in a final volume of 10 µl on ice for 25 min. All binding reactions contained 25 mM Tris-HCl (pH 7.5), 0.05 mM EDTA, 50 mM KCl, 1 mM dithiothreitol, 5% glycerol, and 2 µg of poly(dI:dC). Following electrophoresis in a 6% polyacrylamide gel (acrylamide/bis at 40:1) in Tris-Glycine-EDTA buffer [37 mM Tris-HCl (pH 8.0), 50 mM glycine, 2 mM EDTA] at 10 V/cm for 2 hr, gels were dried and autoradiographed at −70° C. b) EMSA was slightly modified for TFO competition experiments. Ten fmol of end-labeled oligonucleotides (final preincubation concentration 2.5 nM) were incubated with increasing concentrations of Oligo Col TFO (SEQ ID No: 5) and Oligo Control (SEQ ID No: 7) (0 to 25 µM) in 4 µl TFO binding buffer as described above. After 1 h of preincubation at 22° C., 10 µg of RCF nuclear extract were added in a volume of 8 µl containing 25 mM Tris-acetate (pH 6.8), 0.5 mM EDTA, 10 mM $MgCl_2$, 50 mM KCl, 0.5 mM dithiothreitol, 10% glycerol, and 2 µg of poly(dI:dC) resulting in a final volume of 12 µl. Binding reaction was allowed to proceed for 25 min on ice and the reaction mixture was then loaded on the same gel as described above.

EXAMPLE 8

In Vitro Transcription Assay

Twenty ng (30 fmol) of the 1.1-kb collagen fragment, 5 ng (30 fmol) of the 250-bp fragment, isolated from pCol 952/1000 and pCol140, respectively (final preincubation concentration 7.5 nM) and approximately the same concentration of 0.9-kb CMV IE fragment were preincubated in separate reactions with increasing concentrations of Oligo Col TFO (SEQ ID No: 5) (final concentrations from 0 to 250 µM) and Oligo Col TFOa (SEQ ID No: 6) (final concentrations from 0 to 25 µM, and 4 µl of TFO binding buffer. After 1 h preincubation at 22° C., templates were incubated with 11 µl of HeLa nuclear extracts (≈80 µg protein) in a 25 µl reaction mixture containing 10 mM HEPES (pH 7.9), 50 mM KCl, 3 mM $MgCl_2$, 0.2 mM EDTA, 0.25 mM dithiothreitol, 10% glycerol, 0.4 mM ATP, 0.4 mM CTP, 0.4 mM UTP, and 16 µM cold GTP with 130 nM of ($\alpha^{32}$P)GTP for 1 hour at 30° C. The reaction was stopped by adding 175 µl of stop mix [0.3M Tris-HCl (pH 7.4), 0.3M Na-acetate, 0.5% sodium dodecyl sulfate, 2 mM EDTA, 3 µg/ml tRNA], extracted once with phenol, once with phenol/chloroform (1:1), ethanol precipitated, dried, and resuspended in 20 µl of 50% formamide loading dye. The samples were heat-denatured and loaded on a 6% acrylamide, 7M urea gel, ran at 20 V/cm for 2 hr. Gels were directly autoradiographed at −70° C.

EXAMPLE 9

Transient Transfection Experiments

Rat cardiac fibroblasts were maintained in Dulbecco's modified Eagle's medium supplemented with 10% fetal calf serum. The cells were incubated in 8% atmosphere, and plated approximately 24 h before transfection at a density of $0.5 \times 10^6$ cells in 10-cm diameter plastic dishes. Transfection was performed by the lipofectamine method (GIBCO BRL, Grand Island, N.Y.) according to manufacturer's recommnendation. Four µg of ColCAT plasmids and 2 µg of PSV2Gal plasmid (Promega, Madison, Wis.) were preincubated with 20 µl Lipofectine in 300 µl serum free DMEM at room temperature for 30 min. Cells were washed two times with prewarmed DMEM. Then, the preincubated mixture was diluted in DMEM to a final volume of 3 ml and added to plates. Cells were incubated for 2 h at 37° C. Oligonucleotides were preincubated with lipofectamine under the same conditions as the plasmid DNA's, except that the final dilution to 3 ml was done in DMEM supplemented with 3% fetal calf serum. Cells were washed twice, and were incubated in the oligonucleotide containing mixture for 4 h at 37° C. following which the medium was changed to DMEM containing 10% fetal calf serum. Cells were harvested by scraping 24 h after start of transfection in 1 ml solution of 40 mM Tris-HCl (pH 7.5), 1 mM EDTA, 150 mM NaCl. Cells were centrifuged for 1 min in microfuge, and resuspended in 60 µl 0.25M Tris-HCl (pH 7.5). Cell extracts were made by three cycles of freezing and thawing in dry ice-ethanol and 37° C. water bath for 5 min each. Supernatant was removed and protein concentration was measured by the Bradford method (42).

EXAMPLE 10

Assay of Chloramphenicol Acetyl transferase (CAT) and β-galactosidase Activity CAT activity was measured according to Gorman et al. (37). Samples were heated for 10 min at 68° C. prior to assay of CAT activity. Radiolabeled chloramphenicol (0.1 µCi of D-threo-[dichloroacetyl-1-$^{14}$C] chloramphenicol) and 20 µl of 4 mM acetyl coenzyme A were added to samples containing 10 µg of protein and 50 µl of 1 M Tris-HCl (pH 7.8) in a final volume of 100 µl. The samples were incubated for 1.5 h at 37° C., which was within the linear range for these reactions. After ethyl acetate extraction, the chloramphenicol and the acetylated products were separated by thin layer chromatography for 1.5 h in a 95:5 ratio of chloroform to methanol. The thin layer plates were exposed to x-ray film for autoradiography. Acetylated and non-acetylated radioactive areas were removed from the plates and placed into scintillation counting fluid. The radioactivity was quantified by a Beckman scintillation counter. Transfection efficiency was determined by co-transfection with pSV2Gal plasmid (Promega, Madison, Wis.) and P-galactosidase activity was measured as described (38). Briefly, cell extracts containing 5 µg of protein were incubated in 80 mM sodium phosphate buffer (pH 7.4), 102 mM 2-mercaptoethanol, 9 mM $MgCl_2$, and 8 mM CPRG at 37° C. for 2 h. The optical density was measured at 570 nmn.

RESULTS

The −220 to −120 Segment of the α1(I) Collagen Promoter Contains Multiple Binding Sites for Factors Present in RCF Nuclear Extracts In order to identify specific binding proteins in rat cardiac fibroblasts, nuclear extracts were prepared from cultured adult rat cardiac fibroblasts and DNase I footprint analysis was carried out as described using a BglII-HaeIII restriction fragment of SEQ ID No: 4 of the α1(I) collagen promoter (−225 to −123), labeled at the −223 position on the non-coding strand (FIG. 1, asterisk). Five areas of protection designated a through f are seen (FIG. 2, lanes 3–4). The corresponding nucleotide sequences are underlined in FIG. 1. The protected areas a and b are part of the 35-bp long polypyrimidine region, areas d, e, and f correspond to the purine-rich sequence distal to the polypyrimidine region, and the protected area c is an interconnecting sequence between the two. Examination of the sequences protected by nuclear factors revealed that among the different areas, the complementary sequence to AAAGGG of area f can be found in areas b and a; furthermore the complementary sequence to GGAGG of area e is present in area a. These results indicate that multiple binding sites are present within the −200 to −120 region of the α1(I) collagen promoter that form complexes with protein factor(s) present in the RCF as well as HeLa cell nuclear extracts. It is important to note that many of these binding sequences, especially binding site a, b, and c, are highly conserved among species (25) indicating the functional importance of these elements in the regulation of collagen gene expression.

The Polypyrimidine and Purine-rich Elements Bind More than One Factor

Figure 3:
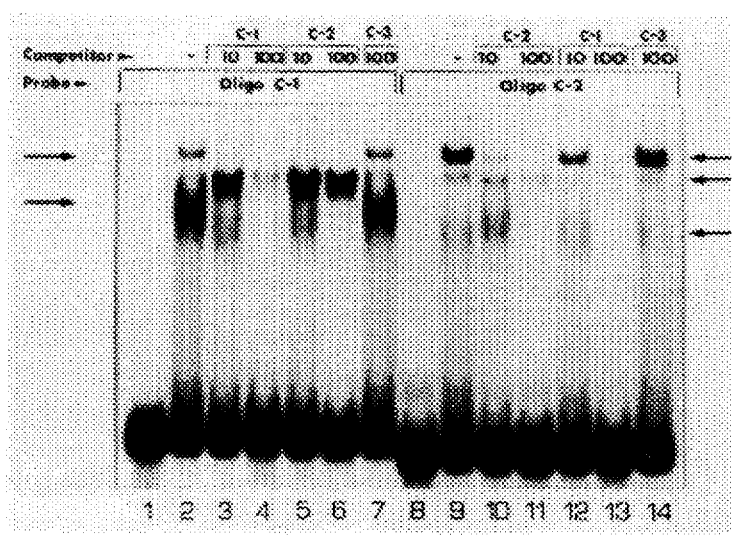
FIG. 3 shows an autoradiogram of a gel illustrating binding of RCF nuclear factors to Oligo C-1 (SEQ ID No: 1) and Oligo C-2 (SEQ ID No: 2) regions of the rat α1(I) collagen promoter. DNA binding was analyzed by EMSA. Labeled double-stranded Oligo C-1 (SEQ ID No: 1) (lanes 1–7) and Oligo C-2 (SEQ ID No: 2) (lanes 8–14) were incubated with nuclear extracts of RCF (except for lanes 1 and 8 where BSA was used) and fractionated on a 6% polyacrylamide gel. Competition experiments were performed with increased amounts of unlabeled Oligo C-1 (SEQ ID No: 1) (lanes 3, 4, 12, and 13), Oligo C-2 (SEQ ID No: 2) (lanes 5, 6, 10, and 11), and Oligo C-3 (SEQ ID No: 3) (lanes 7 and 14). Arrows indicate the slow-migrating protein-DNA complexes.

In order to better characterize the protein-DNA interactions within these footprinted segments of the α1(I) promoter, double-stranded oligonucleotides corresponding to the −170 to −141 polypyrimidine sequence (designated Oligo C-1 and SEQ ID No: 1), and to the −197 to −173 purine-rich sequence (designated Oligo C-2 and SEQ ID No: 2) were synthesized and used in electrophoretic mobility shift assays. A farther upstream sequence (designated Oligo C-3 and SEQ ID No: 3) was also used as a control in competition experiments. The location and the sequences of these oligonucleotides are shown in FIG. 1. In earlier work by Karsenty & de Crombrugghe (27), oligonucleotide sequences contained within the mouse α1(I) collagen promoter corresponding to Oligo C-1 (SEQ ID No: 1) and Oligo C-2 (SEQ ID No: 2) were used in electrophoretic mobility shift assays, and were found to bind the same factor present in NIH-3T3 cell nuclear extracts. Transient transfection experiments using substitution mutations of the nucleotides labeled with vertical arrows in FIG. 1 indicated that this factor acted as a transcriptional inhibitor. It is of note that while the sequence of Oligo C-1 (SEQ ID No: 1) is identical in rat and mouse, the purine-rich Oligo C-2 (SEQ ID No: 2) shows only about 80% homology between these two species. The results of the EMSA's in this study are shown in FIG. 3. Oligonucleotides C-1 (SEQ ID No: 1) and C-2 (SEQ ID No: 2) were end-labeled and incubated with RCF nuclear extracts as described. Using Oligo C-1 (SEQ ID No: 1) as a probe, two distinct slow-migrating bands, indicating the formation of DNA-protein complexes, are seen (FIG. 3, lane 2, see arrows on left). The incubation of Oligo C-2 (SEQ ID No: 2) probe with nuclear extract resulted in three slow-migrating complexes (FIG. 3, lane 9, arrows on right). Competition experiments showing inhibition of complex formation by the use of 10- and 100-fold molar excess of unlabeled C-1 (SEQ ID No: 1) and C-2 (SEQ ID No: 2) oligonucleotides with their respective probes demonstrate the specificity of these complexes (FIG. 3, lanes 3–4, and 10–11). This is further supported by the fact that the Oligo C-3 (SEQ ID No: 3) was unable to inhibit the formation of any of these complexes (FIG. 3, lanes 7 and 14). Looking at the mobility and the pattern of the complexes, it is interesting to note that the sharper top bands in lanes 2 and 9 migrate at the same position, while the mobility of the more diffuse lower bands is different. Furthermore, the pattern of competition indicates that the affinity of protein-DNA binding may be different within the various complexes, as evidenced by complete inhibition of the top complexes at ten times lower molar excess of the respective competitors than is seen with the lower complexes.

Substantial homology exists in the sequences of the different binding sites as discussed above. The experiments of Karsenty & de Crombrugghe (27) suggested the presence of a single negative regulatory factor in NIH-3T3 cell nuclear extracts that bind to both oligonucleotides of the mouse promoter corresponding to Oligo C-1(SEQ ID No: 1) and C-2 (SEQ ID No: 2). Therefore, cross-competition experiments were performed using unlabeled Oligo C-1 (SEQ ID No: 1) to compete with the binding of labeled Oligo C-2 (SEQ ID No: 2) and vice versa (FIG. 3, lanes 5–6, and 12–13). The results show that Oligo C-1 (SEQ ID No: 1) was able to completely compete with the binding of all three complexes to Oligo C-2 (SEQ ID No: 2) probe (FIG. 3, lanes 12–13) indicating that Oligo C-1 (SEQ ID No: 1) contains all the elements required for binding of nuclear factors to Oligo C-2 (SEQ ID No: 2). Once again, a differential competition pattern among the three complexes can be seen [the middle complex is competed at lower molar excess of Oligo C-1 (SEQ ID No: 1) than the top and lower ones]. By contrast, when unlabeled Oligo C-2 (SEQ ID No: 2) was used to compete with the binding of nuclear factors to Oligo C-1 (SEQ ID No: 1) probe, complete competition was not seen (FIG. 3, lanes 5–6). Only the slower mobility higher complex was competed, and the lower complex showed no inhibition. In fact, it would appear that in the presence of unlabeled Oligo C-2 (SEQ ID No: 2), the binding of Oligo C-1 (SEQ ID No: 1) to nuclear factor(s) becomes more compact and slightly shifted. The results suggest that Oligo C-2 (SEQ ID No: 2) does not contain all elements necessary for the formation of complexes like Oligo C-1 (SEQ ID No: 1). It is also possible that Oligos C-1 (SEQ ID No: 1) and C-2 (SEQ ID No: 2) may contain some closely related elements that have different binding affinities to the same protein factor. To consider different alternatives, further studies will be required using substitution mutations in the various binding elements and the purification and cloning of factors involved in the formation of complexes with these elements.

Oligonucleotides Col TFO (SEQ ID No: 5), Col TFOa (SEQ ID No: 6), 147 P (SEQ ID No: 8), 170 APS (SEQ ID No: 9), 164 AP (SEQ ID No: 10), 164 APS (SEQ ID No: 1), and 158 APS (SEQ ID No: 12) Form Triple-Helix Structure with Oligo C-1 (SEQ ID No: 1)

Figure 4:
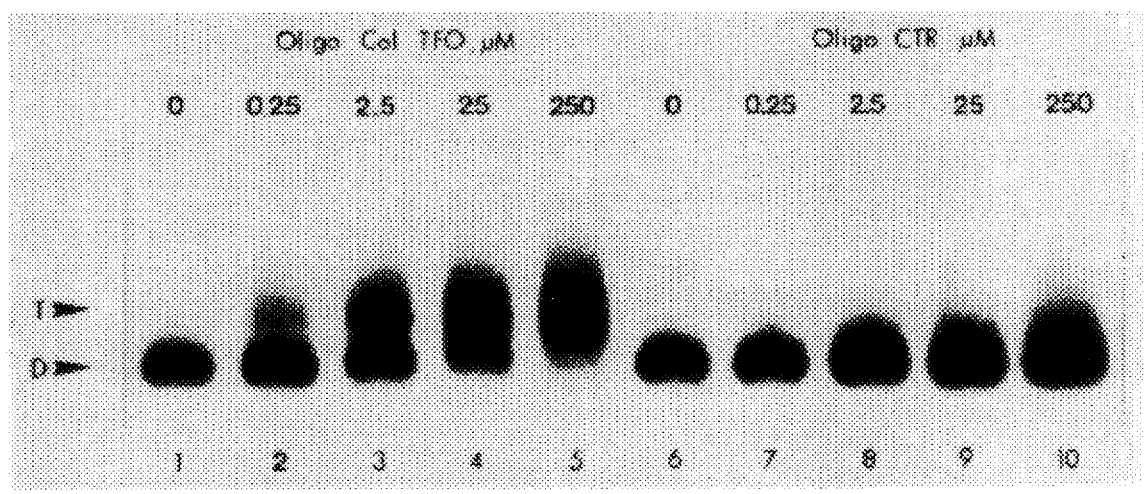
FIG. 4. shows an autoradiogram of a gel illustrating the results of a gel mobility shift analysis of oligonucleotide-directed triplex formation on the α1(I) collagen promoter target. Double-stranded target oligonucleotide Oligo C-1 (SEQ ID No: 1) was end-labeled and incubated alone (lanes 1 and 6) or with an excess of unlabeled single-stranded Oligo Col TFO (SEQ ID No: 5) (lanes 2–5), and Oligo Control (SEQ ID No: 7) (lanes 7–10). The concentration of the oligonucleotide added to approximately 1 nM target DNA is indicated above each lane. D=duplex DNA; T=triplex DNA.

The 35-bp long polypyrimidine sequence from −172 to −138 represents a unique structure in the promotor of the rat α1(I) collagen gene. Such long stretches of all C's and T's do occur in other genes, but only rarely. It was hypothesized that a single-stranded oligonucleotide with a complementary sequence would be able to form a triple-helix DNA structure with the polypyrimidine portion of the collagen promoter as target sequence. In order to demonstrate the formation of triple-helix on target sequence, gel mobility shift assays (39) were performed. The detection of triplex structure in this electrophoresis system is based on the observation that the triple-helix migrates slower as compared to double-stranded oligonucleotide in acrylamide gel due to the reduction of DNA charge that is likely to accompany triplex formation (31). Initial testing of triple-helix formation was performed with the use of single-stranded oligonucleotides with identical sequence to the polypurine strand of Oligo C-1 (SEQ ID No: 1). The sequence and orientation of these oligonucleotides, designated Oligo Col TFO (SEQ ID No: 5) and Oligo Col TFOa (SEQ ID No: 6) are shown in FIG. 1. Radiolabeled double-stranded DNA target (Oligo C-1; SEQ ID No: 1) was incubated with increasing amounts of specific Oligo Col TFO (SEQ ID No: 5), Oligo Col TFOa (SEQ ID No: 6), and Oligo Control (SEQ ID No: 7). The results of the gel mobility shift analysis using Oligo Col TFO (SEQ ID No: 5) and Oligo Control (SEQ ID No: 7) are shown in FIG. 4; Oligo Col TFOa (SEQ ID No: 6) at one-tenth the concentration of Oligo Col TFO (SEQ ID No: 5) gave identical results.

The addition of increasing concentrations of Oligo Col TFO (SEQ ID No: 5) relative to target results in a gradual shift from duplex (D) to a distinct higher-migrating band (T), indicating the formation of triple-helix. This concentration-dependent shift reaches 50% at approximately 1 μM. This corresponds to a 1000-fold molar excess of oligonucleotide to duplex, yielding an approximate dissociation constant $K_d$ of $10^{-6}$M, based on the equation D/T= $K_d \times 1/[\text{Pur}]$, where [Pur] is the final concentration of purine oligonucleotide (31). By contrast Oligo Control (SEQ ID No: 7) failed to form triple-helix as evidenced by the absence of retarded band even at higher concentrations (FIG. 4, lanes 6–10). In summary, the gel mobility shift analysis showed that the single-stranded Oligo Col TFO (SEQ ID No: 5) forms triplex with target Oligo C-1 (SEQ ID No: 1) in a sequence-specific manner within the expected $K_d$ range for triple-helix structures.

In order to pinpoint the regions within Oligo Col TFO (SEQ ID No: 5) and Oligo Col TFOa (SEQ ID No: 6) which are responsible for the triplex formation demonstrated above, five overlapping 18-mer oligonucleotides [Oligo 147 P (SEQ ID No: 8), Oligo 170 APS (SEQ ID No: 9), Oligo 164 AP (SEQ ID No: 10), Oligo 164 APS (SEQ ID No: 11), and Oligo 158 APS (SEQ ID No: 12)] were tested for their ability to form triplexes with Oligo C-1 (SEQ ID No: 1). These five oligonucleotides are described in Table 1, and their sequences and orientations are shown in FIG. 8. Radiolabeled Oligo C-1 (SEQ ID No: 1) was incubated with increasing amounts of each of these five oligonucleotides. The results of this gel mobility shift analysis are shown in FIGS. 9–11.

Figure 9:
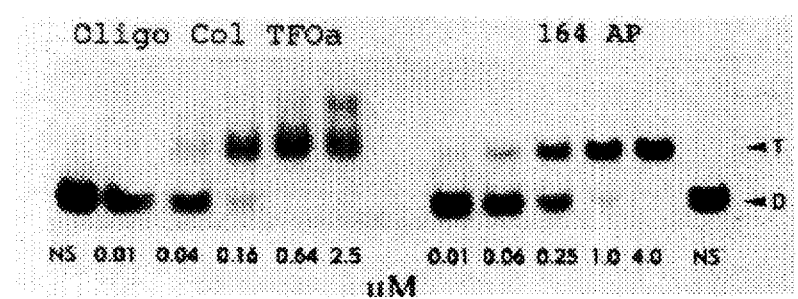
FIG. 9 shows an autoradiogram of a gel illustrating the results of a gel mobility shift analysis of oligonucleotide-directed triplex formation on the α1(I) collagen promoter target. Double-stranded target oligonucleotide Oligo C-1 (SEQ ID No: 1) was end-labeled and incubated with an excess of unlabeled single-stranded Oligo Control (SEQ ID No: 7) (lanes labeled "NS" for nonspecific oligonucleotide), Oligo Col TFOa (SEQ ID No: 6), or Oligo 164 AP (SEQ ID No: 10). The concentration of Oligo Col TFOa (SEQ ID No: 6) or Oligo 164 AP (SEQ ID No: 10) added to approximately 1–2 nM target DNA is indicated below each lane. D=duplex DNA; T=triplex DNA.
Figure 10:
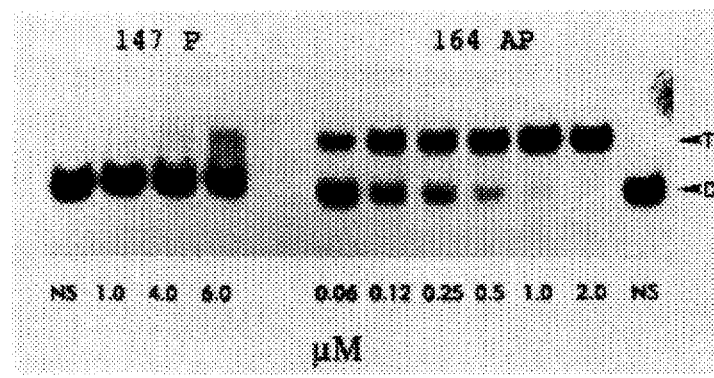
FIG. 10 shows an autoradiogram of a gel illustrating the results of a gel mobility shift analysis of oligonucleotide-directed triplex formation on the α1(I) collagen promoter target. Double-stranded target oligonucleotide Oligo C-1 (SEQ ID No: 1) was end-labeled and incubated with an excess of unlabeled single-stranded Oligo Control (SEQ ID No: 7) (lanes labeled "NS" for nonspecific oligonucleotide), Oligo 147 P (SEQ ID No: 8), or Oligo 164 AP (SEQ ID No: 10). The concentration of Oligo 147 P (SEQ ID No: 8) or Oligo 164 AP (SEQ ID No: 10) added to approximately 1–2 nM target DNA is indicated below each lane. D=duplex DNA; T=triplex DNA.
Figure 11:
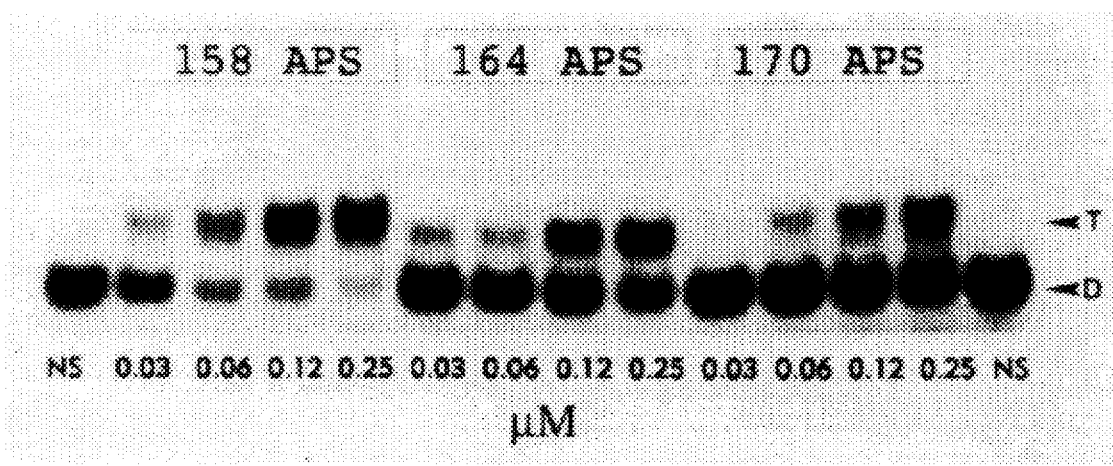
FIG. 11 shows an autoradiogram of a gel illustrating the results of a gel mobility shift analysis of oligonucleotide-directed triplex formation on the α1(I) collagen promoter target. Double-stranded target oligonucleotide Oligo C-1 (SEQ ID No: 1) was end-labeled and incubated with an excess of unlabeled single-stranded Oligo Control (SEQ ID No: 7), Oligo 158 APS (SEQ ID No: 12), Oligo 164 APS (SEQ ID No: 11), or Oligo 170 APS (SEQ ID No: 9). The concentration of Oligo 158 APS (SEQ ID No: 12), Oligo 164 APS (SEQ ID No: 11), or Oligo 170 APS (SEQ ID No: 9) added to approximately 1–2 nM target DNA is indicated below each lane. D=duplex DNA; T=triplex DNA.

The addition of increasing concentrations of each of Oligo 147 P (SEQ ID No: 8), Oligo 170 APS (SEQ ID No: 9), Oligo 164 APS (SEQ ID No: 11), and Oligo 158 APS (SEQ ID No: 12) relative to target again results in a gradual shift from duplex (D) to a distinct higher-migrating band (T), indicating the formation of triple-helix (FIGS. 9–11). As expected, Oligo 147 P (SEQ ID No: 8), the parallel oligonucleotide relative to the purine strand of Oligo C-1 (SEQ ID No: 1), formed a triplex only at high concentrations ($K_d > 10$ μM) (FIG. 10). In contrast, Oligo 164 AP (SEQ ID No: 10), the antiparallel oligonucleotide relative to the purine strand of Oligo C-1 (SEQ ID No: 1), formed a triplex at extremely low concentrations (more than 30% and 50% of the duplex was converted to triplex at 0.06 μM and 0.1 μM, respectively) (FIG. 10).

The results illustrated in FIGS. 9–11 demonstrate that the antiparallel 18-mer oligonucleotides [Oligo 170 APS (SEQ ID No: 9), Oligo 164 AP (SEQ ID No: 10), Oligo 164 APS (SEQ ID No: 11), and Oligo 158 APS (SEQ ID No: 12)] form triplexes at a $K_d$ similar to or identical to the $K_d$ at which the 30-mer Oligo Col TFOa (SEQ ID No: 6) forms a triplex, and that the effective association constant is at least 100 times lower for antiparallel TFO's relative to parallel TFO's. Furthermore, the results illustrated in FIGS. 10 and 11 demonstrate that Oligo 164 APS (SEQ ID No: 11), a phosphorothioate oligonucleotide, forms a stable triplex at approximately the same concentrations at which Oligo 164 AP (SEQ ID No: 10), a phosphodiester oligonucleotide, forms a stable triplex. Moreover, of the three phosphorothioate oligonucleotides tested, Oligo 158 APS (SEQ ID No: 12) forms a triplex at a concentration lower than the concentration at which Oligo 164 APS (SEQ ID No: 11) forms a triplex, while Oligo 170 APS (SEQ ID No: 9) forms a triplex at a concentration slightly higher than the concentration at which Oligo 164 APS (SEQ ID No: 11) forms a triplex (FIG. 11). Thus, the target sequence −114 to −164 (FIG. 1) in the C-1 region is able to form a triplex most efficiently.

Figure 5:
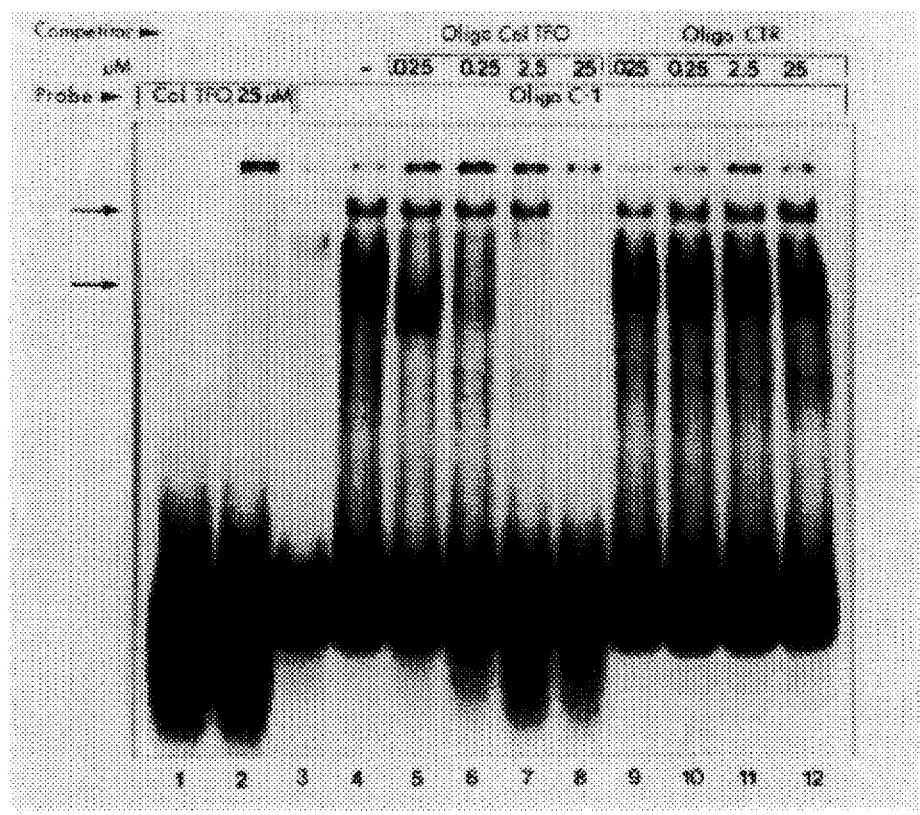
FIG. 5 shows an autoradiogram of a gel illustrating the results of an electrophoretic mobility shift analysis of the effect of triplex-forming oligonucleotide Oligo Col TFO (SEQ ID No: 5) on the binding of protein factor(s) present in RCF nuclear extracts to the target region of the α1(I) collagen promoter. Radiolabeled double-stranded target Oligo C-1 (SEQ ID No: 1) (2.5 nM) (lanes 3–12) was preincubated with increasing concentrations of single-stranded Oligo Col TFO (SEQ ID No: 5) (lanes 5–8), and Oligo Control (SEQ ID No: 7) (lanes 9–12). Samples were then incubated with RCF nuclear extracts (lanes 4–12), and electrophoresed in a polyacrylamide gel. Radiolabeled single-stranded Oligo Col TFO (SEQ ID No: 5) was also incubated with RCF nuclear extracts to exclude binding of protein factors to single-stranded DNA (lane 2). Protein-DNA complexes are indicated by arrows.

Oligonucleotide Col TFO (SEQ ID No: 5) Inhibits the DNA-Protein Interaction Between Oligo C-1 (SEQ ID No: 1) and Protein Factors Present in RCF Nuclear Extracts There is a growing body of evidence that specific triple-helix forming oligonucleotides can effectively inhibit the binding of trans-acting factors to their cis-acting element in a variety of gene promoters both in vitro and in vivo. In order to evaluate the effect of Oligo Col TFO (SEQ ID No: 5) on the binding of nuclear factors contained in RCF nuclear extracts to Oligo C-1 (SEQ ID No: 1), electrophoretic mobility shift assays were performed as described. The conditions were slightly altered to optimize both Oligo Col TFO (SEQ ID No: 5) and protein binding. FIG. 5 shows the results of competition experiments using specific Oligo Col TFO (SEQ ID No: 5) and control oligonucleotide (Oligo Control; SEQ ID No: 7) as competitors for the RCF nuclear protein binding to target oligonucleotide. Increasing amounts of Oligo Col TFO (SEQ ID No: 5) completely eliminated the formation of protein DNA complexes (FIG. 5, lanes 4–8), whereas the control oligonucleotides had no effect on the binding of these factors (FIG. 5, lanes 9–12). To exclude the possibility of protein factors binding to single-stranded oligonucleotide, Oligo Col TFO (SEQ ID No: 5) was end-labeled and incubated with RCF nuclear extract at the highest concentration used in competition experiments. The results (FIG. 5, lane 2) clearly show that inhibition of protein binding in the target region is not due to the ability of Oligo Col TFO (SEQ ID No: 5) to form complexes with the same protein factors. It is interesting to note that specific Oligo Col TFO (SEQ ID No: 5) was able to significantly compete at thirty times less molar excess than that required in titration experiments. Moreover, the two complexes seen in FIG. 5, lane 4 are differentially competed by the specific Oligo Col TFO (SEQ ID No: 5). For instance, approximately hundred times more molar excess of Oligo Col TFO (SEQ ID No: 5) is required to achieve the same level of competition of the upper complex than the lower one. This, once again, supports the notion that factors forming complexes within the target region (Oligo C-1; SEQ ID No: 1) have different binding affinities to their cognate sequences.

Effect of Triplex Formation on α1(I) Collagen Transcription

Figure 6:
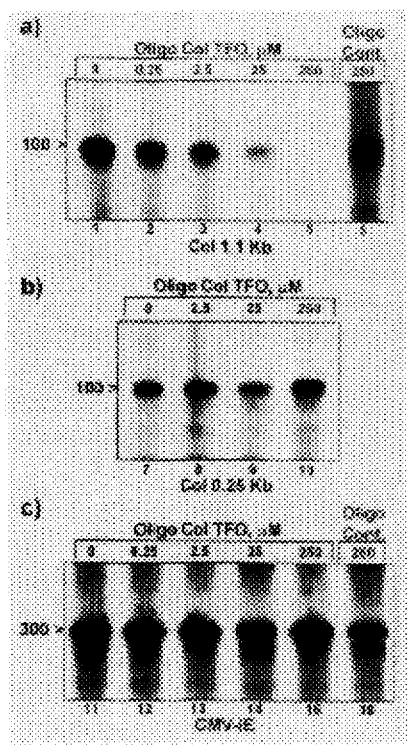
FIGS. 6(a–c) show autoradiograms of gels illustrating the results of an in vitro run-off transcription assay; this assay shows the effect of promoter-targeted triplex-forming Oligo Col TFO (SEQ ID No: 5) on the transcriptional activity of the α1(I) collagen promoter. The −1000 to +100 sequence (lanes 1–6) and the −150 to +100 sequence (lanes 7–10) of the α1(I) collagen gene, and the −600 to +300 fragment of the CMV IE gene (lanes 11–16) were used as templates in in vitro transcription assays. Oligonucleotides at the indicated concentrations were incubated with these templates in separate reactions, followed by HeLa nuclear extract-initiated transcription. Radio-labeled transcription products of expected sizes (100 and 300 nucleotides, respectively) are shown.

The effect of triplex formation and inhibition of protein-factor binding to template on in vitro transcription of α1(I) collagen gene was studied using a HeLa nuclear extract transcription system. The 1.1-kb fragment of the rat α1(I) collagen gene used as template DNA contains 1000-bp of the promoter and 100-bp 3" to the transcription start site. Promoter-dependent run-off transcription generates a 100-nucleotide native α1(I) collagen transcript (FIG. 6, lane 1). Incubation of the collagen template with increasing amounts of triplex-forming Oligo Col TFO (SEQ ID No: 5) resulted in a concentration-dependent inhibition of transcription (FIG. 6, lanes 2–5), whereas the non-triplex-forming Oligo Control (SEQ ID No: 7) had no effect even at the highest concentration used (FIG. 6, lane 6). Also, α1(I) collagen transcription in the presence of Oligo Col TFO (SEQ ID No: 5) does not appear to give rise to increased amounts of RNA transcripts of smaller sizes, suggesting that inhibition of transcription occurs at the level of initiation rather than elongation. To determine the specificity of Oligo Col TFO (SEQ ID No: 5) inhibition of collagen gene transcription, template DNA containing the −136 to +113 sequence, which is downstream from the Oligo Col TFO (SEQ ID No: 5) target site, was used in in vitro transcription under the same conditions. This deleted promoter is sufficient to drive the production of a primary transcript of the same size (approximately 100 nucleotides) (FIG. 6, lane 7). Preincubation of this template with Oligo Col TFO (SEQ ID No: 5) in the same concentration increments resulted in no significant change in the amount of transcript produced (FIG. 6, lanes 8–10). These results suggest that the presence of the polypyrimidine target sequence is required for Oligo Col TFO (SEQ ID No: 5) to inhibit promoter activity.

The effect of oligonucleotides on the transcription process as well as RNA stability was assessed by using the cytomegalovirus immediate early gene as template. Run-off transcription from the CMV IE promoter generates a 300-nucleotide RNA transcript (FIG. 6, lane 11). As shown in lanes 12–16, at the same concentrations which inhibit collagen transcription, Oligo Col TFO (SEQ ID No: 5) has no effect on transcription from the CMV IE promoter under the same assay conditions. The above results, taken together, strongly suggest that inhibition of α1(I) collagen transcription by Oligo Col TFO (SEQ ID No: 5) is due to promoter-targeted triple-helix formation. Oligo Col TFOa (SEQ ID No: 6) at one-tenth the concentration of Oligo Col TFO (SEQ ID No: 5) gave identical results in the in vitro transcription experiments.

Figure 7:
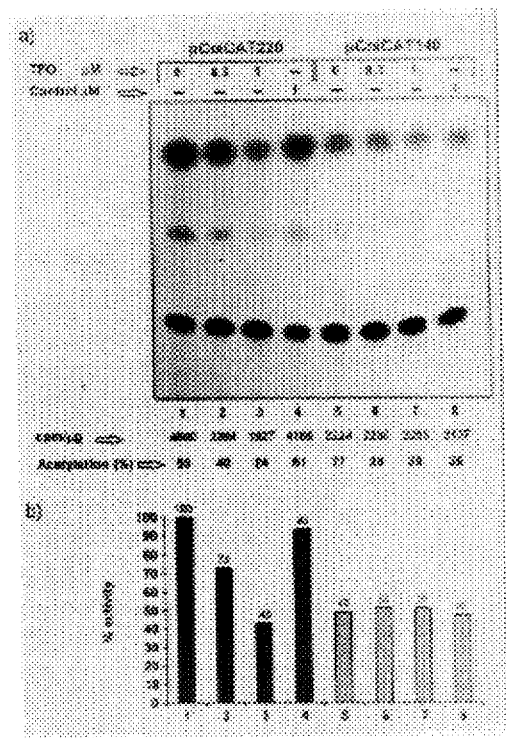
FIGS. 7(a–b) show an autoradiogram of a chromatograph (a) and a histogram (b) which illustrate inhibition of α1(I) collagen promoter-directed transcription by Oligo Col TFO (SEQ ID No: 5) in adult rat cardiac fibroblasts. a) pCol-CAT220 (lanes 1–4) or pColCAT140 (lanes 5–8) reporter constructs were transfected into RCF cells. Two h later cells were re-transfected with Oligo Col TFO (SEQ ID No: 5) or Oligo Control (SEQ ID No: 7) as indicated. Cell lysates were assayed for chloramphenicol acetyl transferase (CAT) activity 24 h later. These data are representative of three independent experiments. Cpm/μg represents the acetylated counts/μg protein. The percentage acetylation was calculated as (radioactivity in the acetylated areas)/(total extracted from thin layer plates)×100.b) Histogram showing the results of transient transfection. After adjusting for β-galactosidase activity to normalize transfection efficiency, the CAT assay counts from treated plates were divided by full activity counts to generate % activity.

Inhibition of a α1(I) Promoter Activity by Oligo Col TFO (SEQ ID No: 5) in Cultured RCF The effect of Oligo Col TFO (SEQ ID No: 5) on the transcriptional activity of the rat α1(I) collagen promoter in cultured cells was investigated. Adult rat cardiac fibroblasts were transiently transfected in separate plates with plasmid pColCAT220, which contains the −225 to +113 sequence of the rat α1(I) gene, and plasmid pColCAT140, in which the TFO target sequence for binding of Oligo Col TFO (SEQ ID No: 5) was deleted. The results indicate that the wild-type and mutant promoters direct expression of the CAT gene. However the expression of pColCAT140 is about 40%–50% of the activity of pColCAT220, suggesting that the −225 to −136 polypurine-polypyrimidine sequence of the α1(I) promoter represents an overall positive regulatory element, confirming the findings of Brenner et al. (28). To demonstrate the effect of oligonucleotides on the expression of these plasmids, cells were allowed to recover from the first transfection, then were re-transfected with oligonucleotides complexed with lipofectamine. As shown in FIG. 7, a dose-dependent inhibition of the CAT activity was observed with Oligo Col TFO (SEQ ID No: 5) on the pColCAT220 construct (FIG. 7, lanes 2–3) whereas the same doses of the Oligo Col TFO (SEQ ID No: 5) have no effect on the deletion mutant pColCAT140 (FIG. 7, lanes 6–7). These results suggest that an intact target sequence is required for Oligo Col TFO (SEQ ID No: 5) to exert its inhibitory effect on the expression of the reporter gene. The specificity of this inhibition is further supported by the fact that Oligo Control (SEQ ID No: 7) had no effect on the expression of either of these plasmids (FIG. 7, lanes 4 and 8). These results on cultured cells parallel the results of the in vitro transcription assays and demonstrate that the interaction of Oligo Col TFO (SEQ ID No: 5) with its target sequence leads to inhibition of transcriptional activity of the rat α1(I) promoter.

DISCUSSION

Two previous studies on the regulatory elements of the α1(I) collagen gene have shed considerable light on the cis-acting elements, trans-acting factors and their functional properties in both in vitro and in vivo experiments. Data from Karsenty & de Crombrugghe (27) have shown two distinct binding sites (from −190 to −170, and from −160 to −133) within the mouse α1(I) collagen promoter. Competition experiments coupled with substitution mutation analyses indicated that the same factor contained in NIH-3T3 nuclear extracts bound to both of these sites. DNA transfection experiments using 3-bp substitution mutants in these polypyrimidine and purine-rich sites suggested that this factor acted as a transcriptional inhibitor (designated IF 1) (27). However, in the studies of Brenner et al., when corresponding sequences were independently deleted, it was found that deletion of the proximal sequence resulted in a 50% reduction of reporter gene activity whereas deletion of the distal element had no significant effect (28). Data provided in the present application confirm the results of Brenner et al. and indicate the presence of multiple binding sites within the sequence −190 to −130. EMSA's identified two distinct complexes bound to Oligo C-1 (SEQ ID No: 1) and three slow-migrating bands when Oligo C-2 (SEQ ID No: 2) was used as probe. These multiple bands could be produced by the interaction of different size proteins with or by the formation of homo or heterodimers. The possible presence of multiple factors and binding elements within these two regions may offer an alternative solution to the seemingly conflicting data shown in the two studies cited, regarding the opposite functional activity of these promoter elements. Karsenty and de Crombrugghe (27) introduced substitution mutations into both proximal and distal elements, while leaving other potentially positive binding elements intact. On the other hand, Brenner et al. (28) used deletion mutations of longer segments of the promoter thereby eliminating the binding of both negative and putative positive trans-acting factors. The discrepancy between these studies may be due to the differences in the promoter sequences. For instance, while the proximal polypyrimidine sequence is identical between rat and mouse α1(I) collagen promoter, the distal polypurine sequence shows only 80% homology.

The advantages of the triplex approach to gene-expression inhibition include fewer and less degenerative targets, thus offering the potential for low-dose long-acting therapeutics. The major limitation of the application of oligomer-directed triplex formation to naturally occurring sequences is the requirement for predominantly polypurine-polypyrimidine regions. The long polypyrimidine sequence of the α1(I) collagen promoter represents a unique structure which provides an attractive target for the design of sequence-specific DNA binding agents, which may influence transcription of this biologically important gene. Although most studies have employed pyrimidine-rich TFO's, in the present study a 30-mer polypurine oligonucleotide corresponding to the noncoding strand of the promoter between −170 and −140 was chosen because of its binding stability at physiological pH. It has been suggested that triplex formation is based on the assembly of G-GC, T-AT, and A-AT triplets (39;41;46). The orientation of the purine type TFO's in the major groove of the double helical DNA has initially been a matter of controversy. In the first description of triplex formation in the promoter of the human c-myc gene, it was implied that the TFO was bound parallel to the purine strand (31). Later evidence suggested that the TFO in that study could potentially bind either parallel or antiparallel and make similar base contacts with the duplex (42). This is because the c-myc target is pseudopalindromic. One TFO used in the present experiments was in the parallel orientation (Oligo Col TFO; SEQ ID No. 5) and another was in the antiparallel orientation (Oligo Col TFOa; SEQ ID No. 6) with the purine strand. Since both of these TFO's have pseudopalindromic sequences, their binding orientation is likely to be antiparallel. This may explain why slightly higher $K_d$ values were observed in gel mobility shift assays using Oligo Col TFO (SEQ ID No: 5). The repression of the in vitro transcription of the collagen promoter by Oligo Col TFO (SEQ ID No: 5) was complete even at lower concentration than was predicted by titration experiments using Oligo Col TFO (SEQ ID No: 5). This difference could be the result of stabilization of the template and the triplex by components of the nuclear extract (e. g., proteins, polyamines). However, the present invention is not limited to any specific manner of binding of an oligomer to a double-stranded DNA.

To evaluate the effect of triple-helix formation on the transcriptional activity of the α1(I) promoter, an in vitro transcription system using HeLa nuclear extracts was employed. HeLa extracts were used instead of extracts from rat cardiac fibroblasts because the latter could not sustain transcription due to an apparent RNase activity unable to be avoided even with the use of RNase inhibitors or different ways of preparing nuclear extracts. The usefulness of the HeLa system in the study of collagen gene expression is supported by the work of Furth et al. (43) who showed that type I collagen mRNAs are accurately initiated by HeLa cell RNA polymerase II. In HeLa cell nuclei, significant amount of collagen mRNA is synthesized. However, steady-state levels of mRNA are not detected, suggesting post-transcriptional regulation of collagen synthesis in HeLa cells. Furthermore, in the study of Brenner et al. (28), DNase I footprints of the more proximal promoter from −103 to −82 showed the same pattern of protection for both HeLa and NIH-3T3 nuclear extracts. DNase I footprinting assays on the promoter fragment from −220 to −120 using HeLa nuclear extract were used. FIG. 2 shows that the protection pattern of HeLa (lanes 5–6) and RCF (lanes 3–4) nuclear extracts is identical, lending further support to the usefulness of the HeLa transcription system. The results of the transient transfection experiments using Oligo Col TFO (SEQ ID No: 5) parallel the findings of the in vitro transcription assays.

The mechanism by which Oligo Col TFO (SEQ ID No: 5)-directed and Oligo Col TFOa (SEQ ID No: 6)-directed triple-helix formation inhibits the transcriptional activity of α1(I) collagen promoter is not entirely clear from the data presented here. One likely possibility is the concentration-dependent interference of Oligo Col TFO (SEQ ID No: 5) with the formation of complexes between cis-acting elements within the target region and their cognate trans-acting factor(s). The ability of triplex-forming oligonucleotides to compete with site-specific DNA-binding proteins for binding to target sites, as the mechanism accounting for transcriptional repression, has been demonstrated in a number of in vitro and in vivo experiments. The close correlation observed in the present study between the ability of Oligo Col TFO (SEQ ID No: 5) to inhibit protein-DNA interaction (FIG. 5) and to repress promoter activity (FIGS. 6 and 7) would support, but not conclusively prove, this mechanism. However, considering that the polypyrimidine target site for Oligo Col TFO (SEQ ID No: 5) has previously been shown to contain elements for binding of a negative trans-acting factor (IF-1) (27), one would expect that inhibition of this factor to bind to its cis-element would result in transcriptional activation. To reconcile these seemingly contradictory findings, the presence of factor(s) with potential positive regulatory activity, and an overall positive transcriptional net effect within this target region could once again be considered. The DNase I footprinting and EMSA data presented here support this notion as does the previously cited result of Brenner et al. (28); additionally, the transient transfection experiment presented here, showing a 50% reduction of promoter activity upon complete deletion of sequences corresponding to the Oligo Col TFO (SEQ ID No: 5) target site, confirms this result of Brenner et al. (28). An alternative explanation for the inhibitory effect of Oligo Col TFO (SEQ ID No: 5) on α1(I) collagen promoter activity could be adopted from the studies by Maher et al. (45) which showed that site-specific DNA triple helices can repress transcription even when the complexes do not overlap transcription-factor binding sites. Their results suggested other possible repression mechanisms including effects on DNA flexibility, recruitment of inhibitory factors or alteration of chromatin structure. The results of in vitro transcription assays presented here, showing complete elimination of promoter activity, as opposed to only partial inhibition that would be expected if protein factor-binding inhibition was primarily operational, support these latter mechanisms.

The identification and characterization of genes which play important roles in cellular processes leading to interstitial fibrosis have provided excellent targets for transcriptional modulation. Because of the ability of TFO's to selectively inhibit transcription of their target genes in intact cells (29;30;32), these oligomers appear to have considerable potential as therapeutic agents. The unique polypyrimidine of the α1(I) collagen promoter was identified as a suitable target for either of two single-stranded polypurine oligonucleotides to form a triple-helix structure that could effectively inhibit transcription in vitro; one of these TFO's, Oligo Col TFO (SEQ ID No: 5), also effectively inhibited transcription in cultured cells. Furthermore, Oligo Col TFOa (SEQ ID No: 6), which is in the antiparallel orientation with the purine strand of the promoter, is ten times more effective in forming a triple-helix structure and in inhibiting in vitro transcription than Oligo Col TFO, which is in the parallel orientation with the purine strand of the promoter.

Additionally, five overlapping 18-mer oligonucleotides [Oligo 147 P (SEQ ID No: 8), Oligo 170 APS (SEQ ID No: 9), Oligo 164 AP (SEQ ID No: 10), Oligo 164 APS (SEQ ID No: 11), and Oligo 158 APS (SEQ ID No: 12)] having sequences found within Oligo Col TFO (SEQ ID No: 5) and Oligo Col TFOa (SEQ ID No: 6) also were able to form triplexes with the C-1 region of the α1(I) collagen-gene promoter. Furthermore, those 18-mer oligonucleotides in the antiparallel orientation relative to the purine strand of the C-1 region [Oligo 170 APS (SEQ ID No: 9), Oligo 164 AP (SEQ ID No: 10), Oligo 164 APS (SEQ ID No: 11), and Oligo 158 APS (SEQ ID No: 12)] formed triplexes as readily as did the 30-mer antiparallel Oligo Col TFOa (SEQ ID No: 6). Moreover, the 18-mer phosphorothioate antiparallel oligonucleotides [Oligo 170 APS (SEQ ID No: 9), Oligo 164 APS (SEQ ID No: 11), and Oligo 158 APS (SEQ ID No: 12)] formed triplexes as readily as the phosphodiester antiparallel oligonucleotides [Oligo Col TFOa (SEQ ID No: 6) and Oligo 164 AP (SEQ ID No: 10)]. Thus, small (i.e., 18-mer), phosphorothioate oligonucleotides are effective in forming triplexes with the C-1 region oligonucleotides. Phosphorothioate oligonucleotides are more resistant to degradation by nucleases than phosphodiester oligonucleotides, and therefore should be more effective for in vivo application. Also, the small size of the 18-mer TFO's makes them a more affordable therapy relative to the 30-mer TFO's.

EXAMPLE 11

Figure 14:
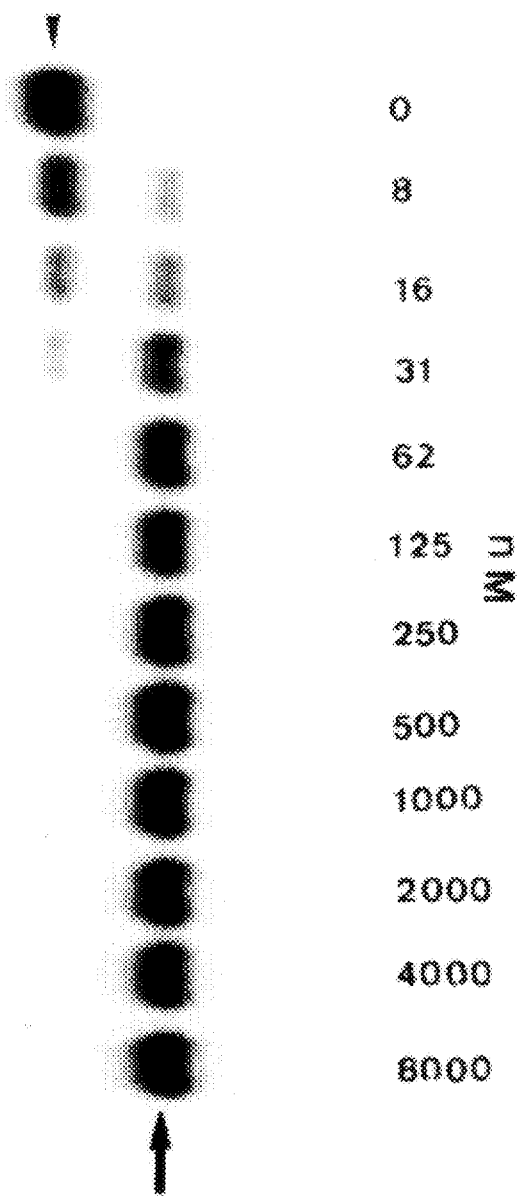
FIG. 14. is an autoradiogram of a gel illustrating the results of a gel mobility shift analysis of oligonucleotide-directed triplex formation on human α1(a) collagen promoter target, where a double-stranded target oligonucleotide (SEQ ID No: 13) was end-labeled and incubated alone (lane 0) and with increasing concentrations of a triplex-forming oligonucleotide (SEQ ID No: 14) to demonstrate triplex formation serving to inhibit expression of the human α1(a) collagen gene.

The double-stranded human collagen genomic DNA promoter sequence from the −165 to −136 portion of the human α1(1) collagen promoter (SEQ ID NO: 13) as well as an anti-parallel human collagen promoter TFO (SEQ ID NO: 14) were prepared as set forth in the preceding examples and were tested for triple-helix formation using the gel mobility shift technique described in Example 4. In particular, the double-stranded human α1(1) promoter oligonucleotide was end-labeled with [α$^{32}$P]ATP using T$_4$ polynucleotide kinase, and was purified through a Sephadex G25 or G50 column. Approximately 5,000 to 10,000 cpm (0.6 ng) was incubated without the TFO (SEQ ID NO: 14) as a control, and with increasing concentrations of the latter ranging from 8 to 8,000 nM in the TFO binding buffer of Example 4. The samples were electrophoresed through 8% polyacrylamide, 0.25% bis-acrylamide gel or 10% polyacrylamide, 0.32% bisacrylamide gel buffered with 89 mM Tris, 89 mM boric acid (pH 7.5) and 20 mM MgCl$_2$ for 4.5 to 7 h at 10 V/cm at 6° C. The gels were then dried and then autoradiographed. The result of this series of tests is set forth in FIG. 14. As shown therein, increasing concentrations of the TFO (SEQ ID NO: 14) generates a gradual shift from the duplex oligonucleotide shown in the control lane to the higher migrating bands, demonstrating the formation of collagen gene expression-inhibiting triple-helix composites.

REFERENCES

1. Abergel, R. P., Mon-Li, C., Bauer, E. A., and Uitto, J. (1987) *J. Invest. Dermatol.* 88, 727–731
2. Brenner, D. A., Veloz, L., Jaenisch, R., and Alcorn, J. M. (1993) *Hepatology* 17, 287–292

3. Downer, G., Phan, S. H., and Wiggins, R. C. (1988) *J. Clin. Invest.* b 82, 998–1006 1006
4. Glick, A. D., Jacobson, H. R., and Haralson, M. A. (1992) *Hum. Pathol.* 23, 1373–1379
5. Madri, J. A., and Furthmayr. (1980) *Hum. Pathol.* 11, 353–359
6. Weber, K. T., Janicki, J. S., Shroff, S. G., Pick, R., Chen, R. M., and Bashey, R. I. (1988) *Circ. Res.* 62, 757–65
7. Chapman, D., Weber, K. T., and Eghbali, M. (1990) *Circ. Res.* 67, 787–94
8. Bishop, J., Greenbaum, J., Gibson, D., Yacoub, M., and Laurent, G. J. (1990) *J. Mol. Cell. Cardiol.* 22, 1157–65
9. Brilla, C. G., Zhou, G., Matsubara, L., and Weber, K. T. (1994) *J. Mol. Cell. Cardiol.* 26, 809–20
10. Weber, K. T. (1994) *News. Physiol. Sci.* 9, 123–28
11. Weber, K. T. (1992) *J. Lab. Clin. Med.* 120, 22–29
12. Weber, K. T., and Brilla, C. G. (1991) *Circulation* 83, 1849–65
13. Rossi, P., Karsenty, G., Robert, A. B., Roche, N. S., Sporn, M. B., and de Crombrugghe, B. (1988) *Cell* 52, 405–14
14. Goldring, M. B., and Krane, S. M. (1987) *J. Biol. Chem.* 262, 16724–29
15. Jimenez, S. A., Freundlich, B., and Rosenbloom, J. (1984) *J. Clin. Invest.* 74, 1112–16
16. Schmidt, A., Setoyama, C., and deCrombrugghe, B. (1985) *Nature* 314, 286–89
17. Penttinen, R. P., Kobayoshi, S., and Bornstein, P. (1988) *Proc. Natl. Acad. Sci. U.S.A.* 85, 1105–8
18. Solis-Herruzo, J. A., Brenner, D. A., and Chojkier, M. (1988) *J. Biol. Chem.* 263, 5841–45
19. Chua, C. C., Chua, B. H. L., Zhao, Z. Y., Krebs, C., Diglio, C., and Perrin, E. (1991) *Connect. Tissue Res.* 26, 271–81
20. Lawrence, W. T., and Diegelmann, R. F. (1994) *Clin. Dermatol.* 12-157–69
21. Sappino, A. P., Schuurch, W., and Gabbiani, G. (1990) *Lab. Invest.* 63, 144–61
22. Slack, J. L., Liska, D. J., and Bornstein, P. (1993) *Am. J. Med. Gen.* 45, 140–51
23. Brenner, D. A., Westwick, J., and Breindl, M. (1993) *Am. J. Physiol.* 264, G589–95
24. de Crombrugghe, B., Vuorio, T., Karsenty, G., Maity, S., Rutheshouser, E. C., and Goldberg, H. (1991) *Ann. Rheum. Dis.* 50 (Suppl 4), 872–76
25. Ravazzolo, R., Karsenty, G., and de Crombrugghe, B. (1991) *J. Biol. Chem.* 266, 7382–87
26. Liau, G., Szapary, D., Setoyama, C., and de Crombrugghe, B. (1986) *J. Biol. Chem.* 261, 11362–68
27. Karsenty, G., and de Crombrugghe, B. (1990) *J. Biol. Chem.* 265, 9934–42
28. Brenner, D. A., Rippe, R. A., and Veloz, L. (1989) *Nucleic Acids Res.* 17, 6055–64
29. Ing, N. H., Beekman, J. M., Kessler, D. J., Murphy, M., Jayaraman, K., Zendegui, J. G., Hogan, M. E., O'Malley, B. W., and Tsai, M.-J. (1993) *Nucleic Acids Res.* 21, 2789–96
30. Grigoriev, M., Praseuth, D., Robin, P., Hemar, A., Saison-Behmoaras, T., Dautry-Varsat, A., Thuong, N. T., Hélène, C., and Harel-Bellan, A. (1992) *J. Biol. Chem.* 267, 3389–95
31. Cooney, M., Czernuszewicz, G., Postel, E. H., Flint, S. J., and Hogan, M. E. (1988) *Science* 241, 456–59
32. Maher, L. J. III., Wold, B., and Dervan, P. B. (1989) *Science* 245, 725–30
33. Lichtler, A., Stover, M. L., Angilly, J., Kream, B., and Rowe, D. W. (1989) *J. Biol. Chem.* 264, 3072–77
34. Sanger, F., Nicklen, S., and Coulson, A. R. (1977) *Proc. Natl. Acad. Sci. U.S.A.* 74, 5463–67
35. Dignam, J. D., Lebovitz, R. M., and Roeder, R. G. (1983) *Nucleic Acids Res.* 11, 1475–89
36. Bradford, M. M. (1976) *Anal. Biochem.* 72, 248–54
37. Gorman, C. M., Moffat, L. F., and Howard, B. H. (1982) *Mol. Cell. Biol.* 2, 1044–1051
38. Eustice, D. C., Feldman, P. A., Colberg-Poley, A. M., Buckery, R. M., and Neubauer, R. H. (1991) *Biotechniques* 11, 739–742
39. Durland, R. H., Kessler, D. J., Gunnell, S., Duvic, M., Pettitt, B. M., and Hogan, M. E. (1991) *Biochemistry* 30, 9246–55
40. Hélène, C., and Toulmé, J.-J. (1990) *Biochim. Biophys. Acta.* 1049, 99–125
41. Kohwi, Y., and Hohwi-Shigematsu, T. (1988) *Proc. Natl. Acad Sci. U.S.A.* 85, 3781–85
42. Durland, R. H., Kessler, D. J., Duric, M., and Hogan, M. In: Pullman, B., Jortner, J., eds. (1990) Boston: Kluwer, 565–578
43. Furth, J. J., Wroth, T. H., and Ackerman, S. (1991) *Exp. Cell. Res.* 192, 118–21
44. Laptev, A. V., Lu, Z., Colige, A., and Prockop, D. J. (1994) *Biochemistry* 33, 11033–11039
45. Maher, L. J. III., Dervan, P. B., and Wold, B. (1992) *Biochemistry* 31, 70–81
46. Frank-Kamenetski, M. D., and Mirkin, S. M. (1995) *Ann. Rev. Biochem.* 64, 65–95

---

We claim:

1. The oligonucleotide of SEQ. ID No. 14.

2. An oligonucleotide having from about 5–50 oligonucleotides and being capable of specifically binding with a double stranded promoter region of α1(I) human collagen gene to form a triple-helix complex.

3. An oligonucleotide which specifically binds with the promoter region of human α1(I) collagen gene to form a triplex with the promoter region in gel mobility shift assay.

4. The oligonucleotide of claim 3, said oligonucleotide binding in an anti-parallel orientation with said promoter region.

5. The oligonucleotide of claim 3, said oligonucleotide having a length of from about 5–50 nucleotides.

6. The oligonucleotide of claim 3, said oligonucleotide comprising SEQ ID No. 14.

* * * * *

UNITED STATES PATENT AND TRADEMARK OFFICE
CERTIFICATE OF CORRECTION

PATENT NO. : 5,780,611
DATED : July 14, 1998
INVENTOR(S) : Ramareddy V. Guntaka, Karl Theodore Weber, Atilla Kovacs, and Jagannadhachari Kandala It is certified that error appears in the above-identified patent and that said Letters Patent is hereby corrected as shown below:

Column 27,
Line 52, please delete the second occurance of "oligo."

Signed and Sealed this

Second Day of October, 2001

Attest:

NICHOLAS P. GODICI
Attesting Officer     Acting Director of the United States Patent and Trademark Office